United States Patent [19]

Komatsu et al.

[11] Patent Number: 5,436,374
[45] Date of Patent: Jul. 25, 1995

[54] PROCESS FOR PRODUCING 4-FORMYL-4'-METHYLBIPHENYL FROM BIPHENYL

[75] Inventors: Makoto Komatsu, Tsukuba; Susumu Fujiyama, Niigata; Koichi Kida; Mitsuharu Kitamura, both of Tsukuba, all of Japan

[73] Assignee: Mitsubishi Gas Chemical Company, Inc., Tokyo, Japan

[21] Appl. No.: 281,126

[22] Filed: Jul. 28, 1994

[30] Foreign Application Priority Data

Jul. 29, 1993 [JP] Japan ................. 5-188219

[51] Int. Cl.$^6$ ......................... C07C 45/49
[52] U.S. Cl. ..................... 568/428; 568/426; 568/429
[58] Field of Search ............ 568/426, 428, 429

[56] References Cited

U.S. PATENT DOCUMENTS 4,460,794 7/1984 Fujiyama et al. .......... 568/428

FOREIGN PATENT DOCUMENTS 2422197 11/1974 Germany ................. 568/428
25581164 7/1976 Germany ................. 568/428
2155921 10/1985 United Kingdom .

Primary Examiner—Werren B. Lone
Attorney, Agent, or Firm—Armstrong, Westerman, Hattori, McLeland & Naughton

[57] ABSTRACT

A process for producing a 4-formyl-4'-methylbiphenyl from a biphenyl which comprises conducting the carbonylation of the biphenyl with carbon monoxide in the presence of a HF-BF$_3$ catalyst in a carbonylation reactor to obtain the resulting reaction product solution containing a 4-formylbiphenyl, separating the 4-formylbiphenyl from the reaction product solution, hydrogenating the separated 4-formylbiphenyl to obtain a 4-methylbiphenyl, recycling the 4-methylbiphenyl to the carbonylation reactor, and then conducting both the carbonylation of the biphenyl with carbon monoxide to obtain a formylbiphenyl and the carbonylation of the 4-methylbiphenyl with carbon monoxide to obtain a 4-formyl-4'-methylbiphenyl simultaneously in the presence of the HF-BF$_3$ catalyst in the carbonylation reactor.

5 Claims, 1 Drawing Sheet

PROCESS FOR PRODUCING 4-FORMYL-4'-METHYLBIPHENYL FROM BIPHENYL

BACKGROUND OF THE INVENTION

1. Field of the Invention

The present invention relates to a process for producing a 4-formyl-4'-methylbiphenyl, which will be hereinafter referred to as MBPAL, as a precursor of 4, 4'-biphenyldicarboxylic acid.

4, 4'-biphenyldicarboxylic acid (hereinafter referred to as BPDC) which is obtained by oxidation of MBPAL, is a useful raw material for high performance polyester resin or aramide resin having a good heat resistance and a high strength.

2. Related Prior Art

Hitherto, various processes for producing have been proposed for production of BPDC. However, since the so far proposed processes are complicated or provide a low yield, they are actually not economical processes for producing BPDC.

GB 2155921 has proposed a process for producing BPDC which comprises reacting a 4-alkylbiphenyl with carbon monoxide in the presence of a HF-BF$_3$ catalyst to obtain a 4-alkyl-4'-formylbiphenyl in a high yield and then oxidizing the thus obtained 4-alkyl-4'-formylbiphenyl with a gas containing molecular oxygen.

In the process of GB 2155921, 4-alkyl-4'-formylbiphenyl is obtained in a high yield using 4-alkylbiphenyl as a raw material. However, 4-alkylbiphenyl is not a raw material commercially available in a low price. Accordingly, for example, it is required that a biphenyl is carbonylated to synthesize a 4-formylbiphenyl and then the thus synthesized 4-formylbiphenyl is hydrogenated to produce a 4-methylbiphenyl. In case of producing MBPAL by applying the process according the GB 2155921, since the process requires many reaction steps including carbonylation of biphenyl, recovery of HF-BF$_3$ catalyst, separation of 4-formylbiphenyl and its hydrogenation, carbonylation of 4-methylbiphenyl and separation MBPAL, the apparatus for production is complicated and an amount for use of utility becomes large.

SUMMARY OF THE INVENTION

As a result of an extensive study of the above-mentioned subjects in producing MBPAL by the process according to GB 2155921, the present inventors have found unexpectedly that both carbonylation of biphenyl and carbonylation of 4-methylbiphenyl can be conducted simultaneously in one reactor, whereby the apparatus for production of MBPAL can be simplified and an amount for use of utility can be reduced, and has established the present invention.

That is, the present invention provides a process for producing a 4-formyl-4'-methyl-biphenyl from a biphenyl which comprises:

conducting the carbonylation of the biphenyl with carbon monoxide in the presence of a HF-BF$_3$ catalyst in a carbonylation reactor to obtain the resulting reaction product solution containing a 4-formylbiphenyl, separating the 4-formylbiphenyl from the reaction product solution, hydrogenating the separated 4-formylbiphenyl to obtain a 4-methylbiphenyl, recycling the 4-methylbiphenyl to the carbonylation reactor, then, conducting both the carbonylation of the biphenyl with carbon monoxide to obtain a formylbiphenyl and the carbonylation of the 4-methylbiphenyl with carbon monoxide to obtain a 4-formyl-4'-methylbiphenyl simultaneously in the presence of the HF-BF$_3$ catalyst in the carbonylation reactor.

DETAILED DESCRIPTION OF THE INVENTION

Figure 1:
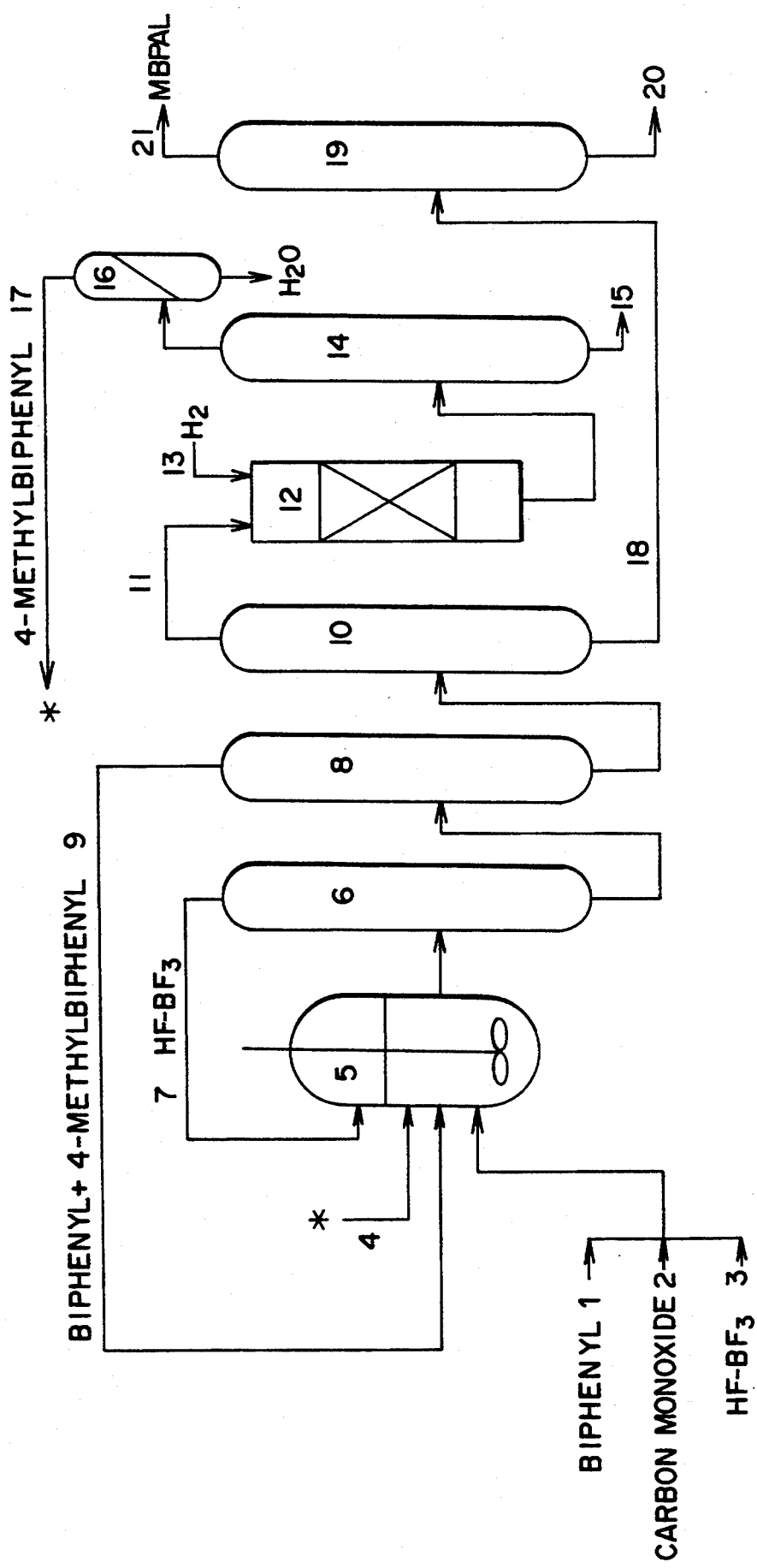
FIG. 1 is a process flow scheme in case of producing MBPAL according to the process of the present invention.

The present invention will be described in detail below.

In case of producing BPDC by oxidation of 4-alkyl-4'-formylbiphenyl, a methyl group among the alkyl groups is most readily and economically changed to a carboxylic group. Therefore, according to the process the present invention, BPDC can be produced with great industrial advantages.

Seemingly, it is easy to conduct two steps-carbonylation simultaneously in one reactor. However, when two reactions different in a raw material are simultaneously conducted in one reactor, the number of components in the product including isomers and side reaction products increases by two times, whereby the separation of the components becomes difficult, and it is necessary to control the balance of reaction velocity between the two reactions. Thus, two reactions different in a raw material cannot be easily conducted simultaneously in one reactor.

That is, when two reactions different in a raw material are simultaneously conducted in one reactor, it is required that the conversion of each reaction and the selectivity including site selectivity should be very high. Likewise, also in the hydrogenation step, a high conversion and a high selectivity are required. By satisfying these requirements two steps-carbonylation can be simulataneously conducted in one reactor.

Since a high conversion and a high selectivity are obtained by employing a HF-BF$_3$ catalyst in the carbonylation reactor according to the present invention, two steps-carbonylation can be simultaneously conducted in one reactor. In order to obtain such high conversion and high selectivity, it is desirable that an amount of HF of at least 10 times to the total moles of biphenyl and 4-methylbiphenyl as raw materials is used and the reaction temperature in carbonylation is −10° C. to 5° C.

According to the present invention, MBPAL is produced by the following steps and thus obtained MBPAL is subjected to oxidation to obtain BPDC.

(I) Carbonylation Step

Both the carbonylation of a biphenyl with carbon monoxide to obtain a 4-formylbiphenyl with carbon monoxide to obtain MBPAL are simultaneously conducted in the presence of a HF-BF$_3$ catalyst in one carbonylation reactor.

(II) Separation Step of Carbonylation Reaction Solution

No-reacted biphenyl and 4-methylbiphenyl are separated from the carbonylation reaction solution in the step I to recycle to the carbonylation reactor and then 4-formylbiphenyl and MBPAL are separated from the carbonylation reaction solution.

(III) Hydrogenation Step 4-formylbiphenyl separated in the step II is reacted with hydrogen to obtain a 4-methylbiphenyl.

(IV) Separation step of hydrogenation reaction solution 4-methylbiphenyl is separated from the hydrogenation reaction solution in the step III to recycle to the step I. Product water and by-products separated in this step are discharged outside the system.

(V) Refining Step

MBPAL separated in the step II is refined. In this step, high boiling point products in the carbonylation are separated.

In the carbonylation, the reaction temperature is $-20°$ to $40°$ C., preferably $-10°$ to $5°$ C. The partial pressure of carbon monoxide is 2 atm or above, preferably as high as possible, economically 10 to 30 atm.

The amount of HF in the catalyst is 5 to 30 times to the total moles of biphenyl and 4-methylbiphenyl as raw materials, preferably 10 to 20 times. The amount of BF is 1.2 to 3 times to the total moles of biphenyl and 4-methylbiphenyl, preferably 1.3 to 2.0 times. As described above, in order to conduct the two carbonlyations simultaneously in one reactor, it is necessary to obtain a high conversion and a high selectivity for the two carbonlylations. Therefore, it is preferable to conduct the two carbonylations using greatly excessive HF at a low temperature.

In the separation step of the carbonylation reaction product solution, a distillation process is applied. First, a small amount of no-reacted biphenyl and 4-methylbiphenyl is recovered from the reaction product solution to recycle to the carbonylation reactor. Then, 4-formylbiphenyl is separated to transfer to the hydrogenation step. The reaction product solution having a higher boiling point is transferred to the refining step. Then, MBPAL is separated from high boiling point products by distillation to obtain refined MBPAL.

In the hydrogenation step, a one-path flow type of reactor filled a noble metal catalyst for hydrogenation is ordinarily applied. The noble metal catalyst for hydrogenation for use includes a catalyst supported 0.1 to 3% by weight of a noble metal such as platinum or palladium on a carrier such as active carbon, alumina or silica. The amount for use of the catalyst is 0.05 to 2.0 g/g·hr as WHSV (feeding rate of 4-methylbiphenyl per weight of catalyst). The partial pressure of hydrogen is 5 to 50 atm, preferably 10 to 30 atm. The reaction temperature is $100°$ to $250°$ C., preferably $120°$ to $160°$ C. In the hydrogenation, it is necessary to selectively reduce a methyl group to a formyl group. However, when reduction with hydrogen is insufficient, a portion of formyl group is changed only to a carbinol group and a methyl group cannot be sufficiently obtained, whereas when reduction with hydrogen is conducted in excess, one benzene ring in a biphenyl is changed to a cyclohexane ring. Therefore, the most suitable combination of an amount of the catalyst and reaction conditions should be selected. The reaction products in the hydrogenation step contain product water and further a small amount of side reaction products containing 4-biphenylmethanol, etc. Therefore, in the separation step of the hydrogenation reaction solution, the by-products are separated and 4-methylbiphenyl is transferred to the carbonylation step. In this separation step, water and by-products are removed, mainly by distillation separation. In 4-methylbiphenyl to be recycled to the carbonylation step, the content of oxygen-containing components excluding a small amount of no-reacted 4-formylbiphenyl needs to be 0.5% by weight or below. When the content of oxygen-containing components is above 0.5% weight, the loss amount of the HF-BF$_3$ catalyst cannot be neglected.

The process according to the present invention is explained using a drawing below. FIG. 1 shows a process flow scheme in case of producing MBPAL according to the process of present invention. In FIG. 1, a biphenyl as a raw material via flow path 1, carbon monoxide via flow path 2, a HF-BF$_3$ catalyst via flow path 3 and a 4-methylbiphenyl via flow path 4 are introduced to carbonylation reactor 5. In carbonylation reactor 5, a 4-formylbiphenyl is obtained by the reaction of the biphenyl with carbon monoxide and simultaneously MBPAL is obtained by the reaction of the 4-methylbiphenyl with carbon monoxide.

First, the HF-BF$_3$ catalyst is separated from the reaction product solution withdrawn from carbonylation reactor 5 in the HF-BF$_3$ recovery column 6 to recycle to carbonylation reactor 5 via flow path 7. Then, in biphenyl separation column 8, a portion of no-reacted biphenyl and 4-methylbiphenyl is separated from the carbonylation reaction product solution to recycle to carbonylation reactor via flow path 9. The carbonylation reaction product solution after separation of biphenyl is transferred to formyl separation column 10 to separate 4-formylbiphenyl from MBPAL. The 4-formylbiphenyl is transferred to hydrogenation reactor 12 via flow path 11 and thereat hydrogenation is conducted with hydrogen via flow path 13 to convert the 4-formylbiphenyl into a 4-methylbiphenyl.

The reaction product solution from hydrogenation reactor 12 is transferred to 4-methylbiphenyl recovery column 14. Methylbiphenyls having high boiling points are separated via flow path 15 and 4-methylbiphenyl containing water is recovered from the top of the recovery column 14 to transfer to water separation column 16. Then, in water separation column 16, water is separated from 4-methylbiphenyl. The thus recovered 4-methylbiphenyl is recycled to carbonylation reactor 5 via flow paths 17 and 14.

MBPAL from formyl separation column 10 is transferred to refining column 19 via flow path 18. In refining column 19, high boiling point products are separated via flow path 20 and MBPAL as a product is obtained via flow path 21.

PREFERRED EMBODIMENTS OF THE INVENTION

The present invention will be described in detail below, referring to Examples, which show embodiments of the present invention and are not limitative of the present invention.

EXAMPLE 1

A hastelloy autoclave of 500 cc capacity with a stirrer provided with a cooling medium jacket was used as a carbonylation reactor.

15.6 g (0.10 mol) of biphenyl (produced by Kanto Kagaku k.k., special grade reagent) with a purity of 99% by weight and 17.6 g (0.10 mol) of 4-methylbiphenyl (separated by distillation) with a purity of 98% by weight were charged into the reactor, and then 52.1 g (2.60 mol) of HF (produced by Hashimoto Kasei K.K., hydrogen fluoride anhydride) with a purity of 99.9% by weight and 20.4 g (0.30 mol) of BF$_3$ (produced by Hashimoto Kasei K.K., boron trifluoride) with a purity of 99.7% by weight were fed therein from a bomb with stirring and cooling. Then, carbon monoxide was introduced therein from a bomb to conduct carbonylation under a pressure of 18 kg/cm$^2$G. Carbon monoxide absorption discontinued at about 60 minutes after the carbon monoxide introduction, while keeping the reaction temperature at a temperature of 0° to 50° C.

After the completion of the reaction, the reaction solution was poured into ice water, and the oil layer was recovered therefrom, washed with an aqueous alkaline solution and then with water, Then, MBPAL and 4-formyl-biphenyl was recovered therefrom by distillation. The conversion and selectivity were determined by a gaschromatgraphy analysis of the reaction solution. The conversion of biphenyl was 96.8% and the selectivity to 4-formylbipenyl was 99.3% by mole. The conversion of 4-methylbiphenyl was 99.4% and the selectivity to MBPAL was 97.5% by mole. The purity of the thus obtained MBPAL was 99.1% by weight. The MBPAL could be used as a raw material of BPDC. Moreover, the purity of the thus obtained 4-methylbiphenyl was 99.0% by weight or above.

EXAMPLE 2

A fixed bed catalyst reactor filled 5 g of a catalyst supported 0.5% by weight of palladium on a silica carrier was used as a hydrogenation reactor. Hydrogenation of the 4-formylbiphenyl obtained in Example 1 was conducted in the hydrogenation reactor.

5 g/hr of the solution dissolved 10% by weight of 4-formylbiphenyl in a benzene was continuously fed in the hydrogenation reactor, while keep the hydrogen pressure under 10 atm and the reaction temperature at 130° C. Product water was removed from the reaction product solution by phase separation and then benzene was distilled off to obtain 4-methylbiphenyl. The conversion of 4-formylbiphenyl was 99.3% and the selectivity to 4-methylbiphenyl was 99.0% by mole. A small amount of 4-biphenylmethanol and high boiling point products was further contained in 4-methylbiphenyl. Product water was separated from the reaction product solution and then the 4-biphenylmethanol and high boiling point by-products were removed by distillation, whereby 4-methylbiphenyl with a purity of 98% by weight or above was obtained.

The same reaction as in Example 1 was conducted using the thus obtained 4-methylbiphenyl. As a result, almost the same reaction result as in Example 1 was obtained and it was confirmed that 4-methylbiphenyl could be used by recycling.

According to the present invention, 4-formyl-4'-methylbiphenyl (MBPAL) is obtained in a very high yield from readily available biphenyl and carbon monoxide and 4, 4'-biphenyldicarboxylic acid (BPDC) can be produced with industrial advantages.

That is, in the present invention, both biphenyl and 4-methylbiphenyl are simultaneously carbonylated in one reactor, whereby the process for production of BPDC is simplified and an amount for use of utility can be reduced.

What is claimed is:

1. A process for producing a 4-formyl-4'-methylbiphenyl from a biphenyl which comprises:

conducting the carbonylation of the biphenyl with carbon monoxide in the presence of a HF-BF$_3$ catalyst in a carbonylation reactor to obtain the resulting reaction product solution containing a 4-formylbiphenyl, separating the 4-formylbiphenyl from the reaction product solution, hydrogenating the separated 4-formylbiphenyl to obtain a 4-methylbiphenyl, recycling the 4-methylbiphenyl to the carbonylation reactor, then, conducting both the carbonylation of the biphenyl with carbon monoxide to obtain a formylbiphenyl and the carbonylation of the 4-methylbiphenyl with carbon monoxide to obtain a 4-formyl-4'-methylbiphenyl simultaneously in the presence of the HF-BF$_3$ catalyst in the carbonylation reactor.

2. A process according to claim 1, wherein the amount for use of HF is at least 10 times to the total moles of biphenyl and 4-methylbiphenyl as raw materials.

3. A process according to claim 1, wherein the reaction temperature in carbonylation is −10° C. to 5° C.

4. A process according to claim 1, wherein 4-formylbiphenyl is hydrogenated at a reaction temperature of 100° to 250° C. under a partial pressure of hydrogen of 5 to 50 atm in the presence of a noble metal-containing catalyst.

5. A process according to claim 4, wherein the amount of catalyst is 0.05 to 2.0 g/g·hr measured as the feeding rate of 4-methylbiphenyl per weight of catalyst.

* * * * *